US009050286B2

(12) United States Patent
Laporte et al.

(10) Patent No.: US 9,050,286 B2
(45) Date of Patent: *Jun. 9, 2015

(54) USE OF PEPTIDIC VASOPRESSION RECEPTOR AGONISTS

(75) Inventors: Regent Laporte, San Diego, CA (US); Pierre J-M Riviere, San Diego, CA (US)

(73) Assignee: Ferring B.V., Hoofddorp (NL)

( * ) Notice: Subject to any disclaimer, the term of this patent is extended or adjusted under 35 U.S.C. 154(b) by 1424 days.

This patent is subject to a terminal disclaimer.

(21) Appl. No.: 12/673,375

(22) PCT Filed: Aug. 8, 2008

(86) PCT No.: PCT/IB2008/003444
§ 371 (c)(1),
(2), (4) Date: Mar. 7, 2011

(87) PCT Pub. No.: WO2009/037586
PCT Pub. Date: Mar. 26, 2009

(65) Prior Publication Data
US 2011/0237494 A1    Sep. 29, 2011

Related U.S. Application Data

(60) Provisional application No. 60/935,466, filed on Aug. 14, 2007.

(51) Int. Cl.
| | | |
|---|---|---|
| *A61K 38/12* | (2006.01) | |
| *C07K 7/64* | (2006.01) | |
| *A61P 11/00* | (2006.01) | |
| *A61P 9/00* | (2006.01) | |
| *A61P 7/08* | (2006.01) | |
| *A61P 1/00* | (2006.01) | |
| *C07K 7/16* | (2006.01) | |

(52) U.S. Cl.
CPC .. *A61K 38/12* (2013.01); *C07K 7/16* (2013.01)

(58) Field of Classification Search
None
See application file for complete search history.

(56) References Cited

U.S. PATENT DOCUMENTS

| 3,352,843 | A | 11/1967 | Boissonnas et al. |
| 4,483,794 | A | 11/1984 | Barth et al. |
| 4,829,051 | A | 5/1989 | Cort et al. |
| 5,459,236 | A | 10/1995 | Aurell et al. |
| 5,516,795 | A | 5/1996 | Dellaria et al. |
| 6,262,021 | B1 | 7/2001 | Uvnas-Moberg et al. |
| 6,852,697 | B1 | 2/2005 | Mathison et al. |
| 8,148,319 | B2 | 4/2012 | Wisniewski et al. |
| 8,222,202 | B2 | 7/2012 | Laporte et al. |
| 2003/0109670 | A1 | 6/2003 | Olivera et al. |
| 2004/0009550 | A1 | 1/2004 | Moll et al. |
| 2004/0229798 | A1 | 11/2004 | Landry et al. |
| 2009/0054309 | A1 | 2/2009 | Wisniewski et al. |
| 2009/0275522 | A1 | 11/2009 | Wisniewski et al. |
| 2012/0196808 | A1 | 8/2012 | Wisniewski et al. |

FOREIGN PATENT DOCUMENTS

| CS | 235151 | 2/1987 |
| CS | 242062 | 2/1988 |
| EP | 1 027 067 | 9/2004 |
| EP | 1 406 649 | 2/2008 |
| GB | 1 076 984 | 7/1967 |
| RU | 2063979 | 7/1996 |
| RU | 2342949 | 1/2009 |
| WO | WO 88/01163 | 2/1988 |
| WO | WO 89/03393 | 4/1989 |
| WO | WO 91/13092 | 9/1991 |
| WO | WO 99/46283 | 9/1999 |
| WO | WO 02/064740 | 8/2002 |
| WO | WO 03/082334 | 10/2003 |
| WO | WO 03/099862 | 12/2003 |
| WO | WO 2004/030524 | 4/2004 |
| WO | WO 2006/020491 | 2/2006 |
| WO | WO 2007/095021 | 8/2007 |
| WO | WO 2007/144768 | 12/2007 |

OTHER PUBLICATIONS

Mitchell and Hunter ("Editorial II: Vasopressin and its antagonist: what are their roles in acute medical care?", British Journal of Anaesthesia, vol. 99 (2), Aug. 1, 2007, pp. 154-158).*
Yu et al. (Postgrad Med J 2006;82:140-144).*
Mayo Clinic (http://www.mayoclinic.org/diseases-conditions/irritable-bowelsyndrome/basics/definition/con-20024578, copyright 1998-2014, accessed Jun. 11, 2014).*
Mayo Clinic (http://www.mayoclinic.org/diseases-conditions/irritable-bowel-syndrome/basics/treatment/con-20024578, copyright 1998-2014, accessed Jun. 11, 2014).*
Aregenziano et al. (J Thorac Cardiovasc Surg. Dec. 1998;116(6):973-80).*
Altura et al., "A Structure-Activity Basis for Vasotropic Peptide Therapy in Shock", *Adv. Exp. Med. Biol.*, 1972, 21, 399-408.
Altura et al., "Microcirculatory Actions of Polypeptides and Their Use in the Treatment of Experimental Shock", *Adv. Exp. Med. Biol.*, 1970, 8, 239-247.
Barlos et al., "Solid phase synthesis using trityl type side chain protecting groups", *Peptides*, 1992, 283-284.
Bisello et al., "Parathyroid Hormone-Receptor Interactions Identified Directly by Photocross-linking and Molecular Modeling Studies", *J. Biol. Chem.*, 1998, 273, 22498-22505.
Bodansky et al., "Synthesis of Arginine-Containing Peptides through their Ornithine Analogs. Synthesis of Arginine Vasopressin, Arginine Vasotocin, and L-Histidyl-L-phenylalanyl-L-arginyl-L-tryptophylglycine", *J. Am. Chem. Soc.*, 1964, 86(20), 4452-4459.

(Continued)

*Primary Examiner* — Louise Humphrey
*Assistant Examiner* — Tara Martinez
(74) *Attorney, Agent, or Firm* — Fish & Richardson P.C.

(57) ABSTRACT

The present invention relates to the use of novel compounds for the manufacture of a medicament for treatment of inter alia conditions associated with critical care as well as to a method for treatment of said conditions, wherein said compounds are administered. The compounds utilized are represented by the general formula (I), as further defined in the specification.

14 Claims, No Drawings

(56) References Cited

OTHER PUBLICATIONS

Boss et al., "Induction of NFAT-mediated Transcription by $G_q$-coupled Receptors in Lymphoid and Non-lymphoid Cells", *J. Biol. Chem.*, 1996, 271(18), 10429-10432.

Calabi et al., "H and C spectral assignments of an oxytocin-DTPA derivative, a ligand for potential receptor-specific MR1 contrast agents," Magnetic Resonance in Chemistry; 2005; 43(8); 654-657.

Chen, P., "Vasopressin: New Uses in Critical Care", Southwestern Internal Medicine Conference, *The American Journal of the Medical Sciences*, 2002, 324(3), 146-154.

Abstract—XP-002312063, 1 page, 2003.

Dohler, K. D. et al.; "Wirkmechanismen der vasokonstriktiven Therapie der Osophagusvarizenblutung"; Zeitschrift Fur Gastroenterologie, vol. 41, 2003, pp. 1001-1016 (English abstract).

Fukuyama et al., "2- and 4-Nitrobenzenesulfonamides: Exceptionally Versatile Means for Preparation of Secondary Amines and Protection of Amines", *Tetrahedron Lett.*, 1995, 36, 6373-6374.

Grzonka et al., "Study of Pituitary Hormone Analogs for their Inhibitory Properties and Resistance to Carboxyamidopeptidases: [9-L-Proline]oxytocin, [9-L-Glutamic acid]oxytocin, and [8-L-Lysine,9-glycine methylamide]oxytocin", *J. Med. Chem.*, 1974, 17(12), 1294-1298.

Guild et al., "Interactions between neural and hormonal mediators of renal vascular tone in anaesthetized rabbits", *Exp. Physiol.*, 2003, 88(2), 229-241.

'Wikipedia', [online] "Cardiopulmonary resuscitation," 2013, [retrieved on Nov. 25, 2013]. Retrieved from the Internet: http://en.wikipedia.org/wiki/Cardiopulmonary_resuscitation 17 pages.

'Wikipedia', [online] "Terlipressin," 2013, [retrieved on Nov. 25, 2013]. Retrieved from the Internet: http://en.wikipedia.org/wiki/Terlipressin 2 pages.

'Wikipedia', [online] "Vasopressin," 2013, [retrieved on Nov. 25, 2013]. Retrieved from the Internet: http://en.wikipedia.org/wiki/Vasopressin, 17 pages.

Hugenin et al., "Synthèse de l'Orn8-vasopressine et de l'Orn8-oxytocine", Helv. Chim. Acta., 1963, 1669-1676 (Translation Included).

Jolley et al., "Terlipression Infusion in Catecholamine-resistant shock," *Anaesth. Intensive Care. Col.*, 2003, 31:560-564.

Kimbrough et al., "lysine-vasotocin, a Synthetic Analogue of the Posterior Pituitary Hormones Containing the Ring of Oxytocin and the Side Chain of Lysine-vasopressin", *J. Biol. Chem.*, 1961, 236(3), 778-780.

Lauzier et al. "Utilisation de la vasopressine lors du traitement du choc septique; Vasopressin in the treatment of septic shock", *Reanimation*, 2004, 13, 147-153 (with English abstract).

Merrifield, "Solid Phase Peptide Synthesis. I. The Synthesis of a Tetrapeptide", *J. Am. Chem. Soc.*, 1963, 85, 2149-2154.

Mitsunobu, "The Use of Diethyl Azodicarboxylate and Triphenylphosphine in Synthesis and Transormation of Natural Products", *Synthesis*, 1981, 1-28.

Moreau et al., "Comparison of the effect ofteriipression and albumin on arterial blood volume in patients with cirrhosis and tense ascites treated by paracentesis: a radomised pilot study," *Gut*, 2002, 50:90-94.

Morelli et al., "Effects ofterlipression on systemic and regional haemodynamis in catecholamine-treated hyperkinetic septic shock," *Intensive Care Med.*, 2004, 30:597-604.

Reid, I., "Role of Vasopressin Deficiency in the Vasodilation of Septic Shock", *Circulation*, 1997, 95, 1108-1110.

Ruiz-del-Arbol et al., "Paracentesis-induced circulatory dysfunction: mechanism and effect on hepatic hemodynamics in cirrhosis," *Gastroenterology*, Aug. 1997, 113(2):579-86. (abstract only).

Schillinger et al., "Structure Activity Relationship if the Insulin-Like Effects of the Neurophysical Peptide Hormones", *Eur. J Biochem.*, 1972, 27(3), 473-481.

Streitweiser et al., "Introduction to Organic Chemistry", $3^{rd}$ Ed., Macmillan Publishing Co., New York 1995, pp. 564-567.

Terrillon et al., "Synthesis and Characterization of Fluorescent Antagonists and Agonist for Human Oxytocin Vasopression $V_{1a}$ Receptors," *J. Med. Chem.*, 2002, 45:2579-2588.

Vilhardt et al., "Antidiuretic activity and release of Factor VIII by vasopressin analogues", *Eur. J. Pharmacol.*, 1993, 232, 223-226.

Walter, E.; "Therapie des hepatorenalen Syndroms"; Praxis, Schweizerische Rundschau Fur Medizin-Inhalt & Zusammenfassungen, vol. 86, No. 4,1997, Retrieved from the Internet on Jan. 10, 2008   URL:http://www.oraxis.ch/content/1997/04   1997.html> (English Abstracts included).

Wisniewski and Koiodziejczyk, "The efficient synthesis of FMOC-L-homoglutamine", *Oppi Briefs*, 1997, 29(3), 338-341.

Wold et al., "Principal property values for six non-natural amino acids and their application to a structure-activity relationship for oxytocin peptide analogues", *Can. J. Chem.*, 1987, 65(8), 1814-1820.

Peterson. "The Effect of Vasopressin and Related Compounds at $V_{1a}$ and $V_2$ Receptors in Animal Models Relevant to Human Disease." *Basic & Chemical Pharmacology & Technology.* vol. 99. 2006. pp. 96-103.

O'Brien et al. "Terlipressin for norepinephrine-resistant septic shock." *The Lancet.* vol. 359. 2002. pp. 1209-1210.

\* cited by examiner

```
                         SEQUENCE LISTING

<160> NUMBER OF SEQ ID NOS: 12

<210> SEQ ID NO 1
<211> LENGTH: 9
<212> TYPE: PRT
<213> ORGANISM: Artificial Sequence
<220> FEATURE:
<223> OTHER INFORMATION: synthetic polypeptides
<220> FEATURE:
<221> NAME/KEY: VARIANT
<222> LOCATION: 2
<223> OTHER INFORMATION: Xaa = 2-amino-3-cyclohexylpropanoic acid
<220> FEATURE:
<221> NAME/KEY: MOD_RES
<222> LOCATION: 8
<223> OTHER INFORMATION: Xaa = Dbu
<220> FEATURE:
<221> NAME/KEY: DISULFID
<222> LOCATION: (1)...(6)

<400> SEQUENCE: 1

Cys Xaa Ile Gln Asn Cys Pro Xaa Gly
 1               5

<210> SEQ ID NO 2
<211> LENGTH: 9
<212> TYPE: PRT
<213> ORGANISM: Artificial Sequence
<220> FEATURE:
<223> OTHER INFORMATION: synthetic polypeptides
<220> FEATURE:
<221> NAME/KEY: VARIANT
<222> LOCATION: 2
<223> OTHER INFORMATION: Xaa = 2-amino-3-cyclopentylpropanoic acid
<220> FEATURE:
<221> NAME/KEY: MOD_RES
<222> LOCATION: 8
<223> OTHER INFORMATION: Xaa = Dbu
<220> FEATURE:
<221> NAME/KEY: DISULFID
<222> LOCATION: (1)...(6)

<400> SEQUENCE: 2

Cys Xaa Ile Gln Asn Cys Pro Xaa Gly
 1               5

<210> SEQ ID NO 3
<211> LENGTH: 9
<212> TYPE: PRT
<213> ORGANISM: Artificial Sequence
<220> FEATURE:
<223> OTHER INFORMATION: synthetic polypeptides
```

```
<220> FEATURE:
<221> NAME/KEY: VARIANT
<222> LOCATION: 2
<223> OTHER INFORMATION: Xaa = 1-aminocyclobutanecarboxylic acid
<220> FEATURE:
<221> NAME/KEY: MOD_RES
<222> LOCATION: 8
<223> OTHER INFORMATION: Xaa = Dbu
<220> FEATURE:
<221> NAME/KEY: DISULFID
<222> LOCATION: (1)...(6)

<400> SEQUENCE: 3

Cys Xaa Ile Gln Asn Cys Pro Xaa Gly
 1               5

<210> SEQ ID NO 4
<211> LENGTH: 9
<212> TYPE: PRT
<213> ORGANISM: Artificial Sequence
<220> FEATURE:
<223> OTHER INFORMATION: synthetic polypeptides
<220> FEATURE:
<221> NAME/KEY: VARIANT
<222> LOCATION: 2
<223> OTHER INFORMATION: Xaa = 2-amino-3-cyclohexylpropanoic acid
<220> FEATURE:
<221> NAME/KEY: MOD_RES
<222> LOCATION: 8
<223> OTHER INFORMATION: Xaa = 2-amino-5-(isopropylamino)pentanoic acid
<220> FEATURE:
<221> NAME/KEY: DISULFID
<222> LOCATION: (1)...(6)

<400> SEQUENCE: 4

Cys Xaa Ile Asn Asn Cys Pro Xaa Gly
 1               5

<210> SEQ ID NO 5
<211> LENGTH: 9
<212> TYPE: PRT
<213> ORGANISM: Artificial Sequence
<220> FEATURE:
<223> OTHER INFORMATION: synthetic polypeptides
<220> FEATURE:
<221> NAME/KEY: VARIANT
<222> LOCATION: 2
<223> OTHER INFORMATION: Xaa = 2-amino-4,4-dimethylpentanoic acid
<220> FEATURE:
<221> NAME/KEY: MOD_RES
<222> LOCATION: 8
<223> OTHER INFORMATION: Xaa = Dbu
<220> FEATURE:
<221> NAME/KEY: DISULFID
<222> LOCATION: (1)...(6)

<400> SEQUENCE: 5

Cys Xaa Ile Gln Asn Cys Pro Xaa Gly
 1               5

<210> SEQ ID NO 6
<211> LENGTH: 9
<212> TYPE: PRT
<213> ORGANISM: Artificial Sequence
<220> FEATURE:
<223> OTHER INFORMATION: synthetic polypeptides
<220> FEATURE:
<221> NAME/KEY: MOD_RES
<222> LOCATION: 8
<223> OTHER INFORMATION: Xaa = Dbu
<220> FEATURE:
<221> NAME/KEY: DISULFID
<222> LOCATION: (1)...(6)
```

```
<400> SEQUENCE: 6

Cys Leu Ile Gln Asn Cys Pro Xaa Gly
1               5

<210> SEQ ID NO 7
<211> LENGTH: 8
<212> TYPE: PRT
<213> ORGANISM: Artificial Sequence
<220> FEATURE:
<223> OTHER INFORMATION: synthetic polypeptides
<220> FEATURE:
<221> NAME/KEY: VARIANT
<222> LOCATION: 2
<223> OTHER INFORMATION: Xaa = 1-aminocyclobutanecarboxylic acid
<220> FEATURE:
<221> NAME/KEY: DISULFID
<222> LOCATION: (1)...(6)

<400> SEQUENCE: 7

Cys Xaa Ile Asn Asn Cys Pro Gly
1               5

<210> SEQ ID NO 8
<211> LENGTH: 8
<212> TYPE: PRT
<213> ORGANISM: Artificial Sequence
<220> FEATURE:
<223> OTHER INFORMATION: synthetic polypeptides
<220> FEATURE:
<221> NAME/KEY: VARIANT
<222> LOCATION: 2
<223> OTHER INFORMATION: Xaa = 2-amino-3-cyclopentylpropanoic acid
<220> FEATURE:
<221> NAME/KEY: DISULFID
<222> LOCATION: (1)...(6)

<400> SEQUENCE: 8

Cys Xaa Ile Asn Asn Cys Pro Gly
1               5

<210> SEQ ID NO 9
<211> LENGTH: 9
<212> TYPE: PRT
<213> ORGANISM: Artificial Sequence
<220> FEATURE:
<223> OTHER INFORMATION: synthetic polypeptides
<220> FEATURE:
<221> NAME/KEY: VARIANT
<222> LOCATION: 2
<223> OTHER INFORMATION: Xaa = 1-aminocyclobutanecarboxylic acid
<220> FEATURE:
<221> NAME/KEY: MOD_RES
<222> LOCATION: 8
<223> OTHER INFORMATION: Xaa = Dbu
<220> FEATURE:
<221> NAME/KEY: DISULFID
<222> LOCATION: (1)...(6)

<400> SEQUENCE: 9

Cys Xaa Ile Gln Asn Cys Pro Xaa Gly
1               5

<210> SEQ ID NO 10
<211> LENGTH: 9
<212> TYPE: PRT
<213> ORGANISM: Artificial Sequence
<220> FEATURE:
<223> OTHER INFORMATION: synthetic polypeptides
```

```
<220> FEATURE:
<221> NAME/KEY: VARIANT
<222> LOCATION: 2
<223> OTHER INFORMATION: Xaa = 2-amino-3-cyclopentylpropanoic acid
<220> FEATURE:
<221> NAME/KEY: MOD_RES
<222> LOCATION: 8
<223> OTHER INFORMATION: Xaa = Dbu
<220> FEATURE:
<221> NAME/KEY: DISULFID
<222> LOCATION: (1)...(6)

<400> SEQUENCE: 10

Cys Xaa Ile Asn Asn Cys Pro Xaa Gly
1               5

<210> SEQ ID NO 11
<211> LENGTH: 8
<212> TYPE: PRT
<213> ORGANISM: Artificial Sequence
<220> FEATURE:
<223> OTHER INFORMATION: synthetic polypeptides
<220> FEATURE:
<221> NAME/KEY: VARIANT
<222> LOCATION: 2
<223> OTHER INFORMATION: Xaa = 2-amino-3-cyclohexylpropanoic acid
<220> FEATURE:
<221> NAME/KEY: DISULFID
<222> LOCATION: (1)...(6)

<400> SEQUENCE: 11

Cys Xaa Ile Asn Asn Cys Pro Gly
1               5

<210> SEQ ID NO 12
<211> LENGTH: 9
<212> TYPE: PRT
<213> ORGANISM: Artificial Sequence
<220> FEATURE:
<223> OTHER INFORMATION: synthetic polypeptides
<220> FEATURE:
<221> NAME/KEY: VARIANT
<222> LOCATION: 2
<223> OTHER INFORMATION: Xaa = 2-amino-3-cyclohexylpropanoic acid
<220> FEATURE:
<221> NAME/KEY: MOD_RES
<222> LOCATION: 8
<223> OTHER INFORMATION: Xaa = Dbu
<220> FEATURE:
<221> NAME/KEY: DISULFID
<222> LOCATION: (1)...(6)

<400> SEQUENCE: 12

Cys Xaa Ile Gln Asn Cys Pro Xaa Gly
1               5
```

USE OF PEPTIDIC VASOPRESSION RECEPTOR AGONISTS

This application is a National Stage Application of PCT/IB2008/03444, filed 8 Aug. 2008, which claims benefit of U.S. Ser. No. 60/935,466, filed 14 Aug. 2007 and which applications are incorporated herein by reference. To the extent appropriate, a claim of priority is made to each of the above disclosed applications.

FIELD OF THE INVENTION

The present invention relates to the use of novel compounds for the manufacture of a medicament for treatment of inter alia conditions associated with critical care as well as to a method for treatment of said conditions, wherein said compounds are administered.

BACKGROUND

Peptidic vasopressin V1a receptor agonists, such as terlipressin, have recently (see e.g. O'Brian et al., Lancet 359 (9313):1209-10, Jun. 4, 2002) received increased attention for clinical use in treatment of critical care diseases and conditions, including shock of hypovolemic (e.g. hemorrhagic) or vasodilatory (e.g. septic) origin, bleeding esophageal varices (BEV), hepatorenal syndrome (HRS), cardiopulmonary resuscitation and anesthesia-induced hypotension. They have also been shown to have clinical use in the treatment of orthostatic hypotension, paracentesis-induced circulatory dysfunction, intra-operative blood loss and blood loss associated with burn débridement and epistaxis, and for treatment of various ocular diseases by increasing lacrimation/tear formation.

In treating critical care conditions it is highly desirable to control the arterial blood pressure, and the drug used is typically administered intravenously. Continuous intravenous drug infusion at increasing or decreasing rates is a practical means of providing the desired degree of control. The attainment of so-called "steady state" plasma concentrations of drug depends on the elimination half life of the drug infused. It is generally recognised that steady state plasma concentration is achieved after a period of time equivalent to three times the elimination half life of the drug. To be practical in a clinical setting the desired arterial blood pressure at the steady state should be attained in about two hours, preferably in one hour or less. V1a agonists with an elimination half life longer than 1 hour are therefore usually not considered useful for critical care treatment.

A disadvantage of terlipressin in many critical care situations is its long duration of action, which makes it difficult to titrate its effect as the disease state changes. Terlipressin metabolites have agonist activity at the human V1a (hV1a) receptor.

Also the compound known as F180 (cf. example 3 in U.S. Pat. No. 5,459,236) has an inconveniently long duration of action to be considered for the treatment of most critical care conditions.

Non-specific receptor agonist activity is the main disadvantage of other existing compounds, e.g. [Phe2,Orn8]OT (cf. example if in U.S. Pat. No. 3,352,843) and arginine-vasopressin (AVP). Activity at related receptors such as V1b, V2 and oxytocin (OT) receptors may potentially generate undesirable side effects and safety concerns. As an example, V2 receptor activation may induce antidiuresis (cf. desmopressin), release of coagulation/thrombolysis factors, and induce vasodilation/hypotension with reflex tachycardia. The latter side effect may also be induced by OT receptor agonist activity.

It is an objective of the present invention to provide use of compounds especially in the treatment of conditions associated with critical care, as well as providing further uses of said compounds.

DISCLOSURE OF THE INVENTION

The present invention relates to the use of compounds represented by the general formula (I):

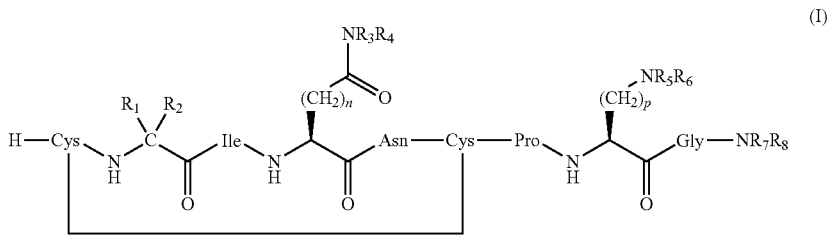

wherein:
$R_1$ is selected from H and part of an alicyclic structure that comprises from 3 to 8 carbon atoms;
$R_2$ is selected from $(CH_2)_m$—X and part of said alicyclic structure;
m is selected from 0, 1, 2 and 3;
n is selected from 0, 1, 2, 3 and 4;
p is selected from 2, 3 and 4;
when $R_1$ is H, $R_2$ is $(CH_2)_m$—X;
when $R_1$ is not H, $R_1$ and $R_2$ together with the α carbon atom to which they are attached form said alicyclic structure;
when m is 0, 2 or 3, X is selected from $C_{3-8}$-cycloalkyl, $C_{5-8}$-cycloalkenyl and $C_{5-8}$-cycloalkynyl;
when m is 1, X is selected from $C_{3-8}$-cycloalkyl, $C_{5-8}$-cycloalkenyl, $C_{5-8}$-cycloalkynyl, isopropyl and tert-butyl; said alicyclic structure, $C_{3-8}$-cycloalkyl, $C_{5-8}$-cycloalkenyl and $C_{5-8}$-cycloalkynyl optionally have at least one alkyl, O-alkyl or hydroxyl substituent;
$R_3$, $R_4$, $R_5$, $R_6$, $R_7$ and $R_8$ are each independently selected from H, alkyl, OH, O-alkyl and OC(O)-alkyl;
alkyl is selected from $C_{1-6}$ straight and $C_{4-8}$ branched chain alkyl and optionally has at least one hydroxyl substituent; and solvates and pharmaceutically acceptable salts thereof;
for the manufacture of a medicament for treatment of hypertensive gastropathy bleeding, sepsis, severe sepsis, septic shock, prolonged and severe hypotension, intradialytic hypotension, cardiac arrest, trauma related blood loss, vasodilatory shock induced by cardiopulmonary bypass, milrinone-induced vasodilatory shock in congestive heart failure, late phase hemorrhagic shock, hepatorenal syndrome type I, cardiovascular instability induced by brain death or anaphylactic shock.

Further uses of the above compounds are for the manufacture of a medicament for treatment of hypotension in severe sepsis, acute respiratory distress syndrome (ARDS) or acute lung injury (ALI).

Still further uses of the above compounds are for the manufacture of a medicament for treatment of inadequate tissue oxygenation, e.g. stemming from nitrogen intoxication (hypoxic lactic acidosis) or carbon monoxide intoxication, shock induced by metformin intoxication, mitochondrial disease or cyanide poisoning, vascular leak syndrome (VLS) induced by interleukin-2 (IL-2) or other cytokines, denileukin diftitox or other immunotoxins, or ovarian hyperstimulation syndrome (OHSS), hypertension induced by end-stage renal disease (ESRD), severe burns, thermal injury, irritable bowel disease (IBD), including Crohn's disease and ulcerative colitis, reperfusion injury (e.g. stemming from thrombotic stroke, coronary thrombosis, cardio-pulmonary bypass, coronary artery bypass graft, limb or digit replantation, organ transplantation, bypass enteritis, bypass arthritis, thermal injury, crush injury/compartment syndrome), infant respiratory distress syndrome (IRDS, RDS), severe acute respiratory syndrome (SARS), ascites, vasodepressor syncope, e.g. vasovagal syncope, postural hypotension with syncope or neurocardiogenic syncope, toxic shock syndrome, idiopathic systemic capillary leak syndrome (Clarkson's disease).

For more detail on the above indications and conditions see e.g. the references Bruha, R. et al. Hepatogastroenterology 49:1161-1166, 2002; Landry, D. W. et al. Circulation 95:1122-1125, 1997; Argenziano, M. et al. Circulation 96:11-286-11-290, 1997; Landry, D. W. et al. U.S. patent application published as no. 2004-229798; Wenzel, V. et al. N. Engl. J. Med. 350:105-113, 2004; Okin, C. R. et al. Obstet. Gynecol. 97:867-872, 2001; Gold, J. et al. Am, J. Cardiol. 85:506-508, 2000; Sharma, R. M. and Setlur, R. Anest. Analg. 101:833-834, 2005; Solanik, P. et al. J. Gastroenterol. Hepatol. 18:152-156, 2000; Yoshioka, T. et al. Neurosurgery 18:565-567, 1986; Kill, C. et al. Int. Arch. Allergy Immunol. 134:260-261, 2004; Westphal, M. et al. Annual Congress of the Society of Critical Care Medicine, Abstract no. 196470, 2006; Landry, D. W. and Oliver, J. A. N. Engl. J. Med. 345 (8):588-595, 2001; Baluna, R. and Vitetta, E. S. Immunopharm. 37:117-132, 1997; Delbaere, A. et al. Endocrine. 26:285-290, 2005; Agarwal, R. Cardiol. Clin. 23:237-248, 2005; Demling, R. H. J. Burn Care Rehabil. 26:207-227, 2005; Bonder, C. S, and Kubes, P. Am. J. Physiol. 284:729-733, 2003; Seal, J. B. and Gewertz, B. L. Ann. Vasc. Surg. 19:572-584, 2005; Zoban, P., Cerny, M. Physiol. Res. 52:507-516, 2003; Bermejo, J. F. and Munoz-Fernandez, M. A. Viral Immunol. 17:535-544, 2004; Arroyo, V. Ann. Hepatol. 1:72-79, 2002; Hainsworth, R. Clin. Auton. Res. 14 Suppl 1:18-24, 2004; Chuang, Y. Y. et al. Paediatr. Drugs. 7:11-25, 2005; Cau, C. Minerva Med. 90:391-396, 1999.

It deserves mentioning that e.g. also isopropyl and 2-n-butyl groups are encompassed by the expression $C_{1-6}$ straight chain alkyl, as said expression is not related to the binding site of the straight chain in question.

$C_{1-6}$ denotes having from one to six carbon atoms, including any number therebetween, and this nomenclature is used analogously herein.

Examples of pharmaceutically acceptable salts comprise acid addition salts, e.g. a salt formed by reaction with hydrohalogen acids, such as hydrochloric acid, and mineral acids, such as sulphuric acid, phosphoric acid and nitric acid, as well as aliphatic, alicyclic, aromatic or heterocyclic sulphonic or carboxylic acids, such as formic acid, acetic acid, propionic acid, succinic acid, glycolic acid, lactic acid, malic acid, tartaric acid, citric acid, ascorbic acid, maleic acid, hydroxymaleic acid, pyruvic acid, p-hydroxybenzoic acid, embonic acid, methanesulphonic acid, ethanesulphonic acid, hydroxyethanesulphonic acid, halobenzenesulphonic acid, toluenesulphonic acid and naphtalenesulphonic acid.

In preferred embodiments $R_7$ and $R_8$ are H. It is especially preferred that $R_3$ and $R_4$ are H.

It is also preferred that n is 1 or 2. Alkyl is typically selected from methyl, ethyl, n-propyl, i-propyl, t-butyl and i-amyl.

X is preferably selected from cyclopentyl and cyclohexyl.

Said alicyclic structure is preferably a cyclobutyl structure.

In the most preferred embodiment of the present use, said compound having the formula (I) is selected from a group consisting of:

(SEQ ID NO: 1)

$$H\text{-Cys-Cha-Ile-Gln-Asn-Cys-Pro-Dbu-Gly-NH}_2; \quad (1)$$

(SEQ ID NO: 2)

$$H\text{-Cys-Ala(cPe)-Ile-Gln-Asn-Cys-Pro-Dbu-Gly-NH}_2; \quad (2)$$

(SEQ ID NO: 3)

$$H\text{-Cys-AcBuc-Ile-Gln-Asn-Cys-Pro-Dbu-Gly-NH}_2; \quad \text{and} \quad (3)$$

(SEQ ID NO: 4)

$$H\text{-Cys-Cha-Ile-Asn-Asn-Cys-Pro-Orn(i-Pr)-Gly-NH}_2. \quad (4)$$

The number in parenthesis denotes the compound as referred to in the following.

The pharmaceutical composition used when practising the present invention may be adapted for oral, intravenous, topical, intraperitoneal, nasal, buccal, sublingual or subcutaneous administration or for administration via the respiratory tract e.g. in the form of an aerosol or an air-suspended fine powder. The composition may thus for instance be in the form of tablets, capsules, powders, microparticles, granules, syrups, suspensions, solutions, transdermal patches or suppositories.

The pharmaceutical composition used may optionally comprise e.g. at least one further additive selected from a disintegrating agent, binder, lubricant, flavoring agent, preservative, colorant and any mixture thereof. Examples of such and other additives are found in "*Handbook of Pharmaceutical Excipients*"; Ed. A. H. Kibbe, $3^{rd}$ Ed., American Pharmaceutical Association, USA and Pharmaceutical Press UK, 2000.

The pharmaceutical composition used is most preferably adapted for parenteral administration. It may comprise a sterile aqueous preparation of the compounds of the invention preferably isotonic with the blood of the recipient. This aqueous preparation may be formulated according to known methods using suitable dispersing or wetting agents and suspending agents. The injectable aqueous formulation Remestyp® (terlipressin) is exemplary of a suitable pharmaceutical formulation type. The preparation may also be a sterile injectable solution or suspension in a diluent or solvent, for example as a solution in 1,3-butane diol. Water, Ringer's solution, and isotonic sodium chloride solution are exemplary acceptable diluents. Sterile, fixed oils may be employed as a solvent or suspending medium. Bland fixed oils, including synthetic mono or di-glycerides, and fatty acids, such as oleic acid, may also be used.

In another embodiment the invention relates to a method for treatment of hypertensive gastropathy bleeding, sepsis, severe sepsis, septic shock, prolonged and severe hypotension, intradialytic hypotension, cardiac arrest, trauma related blood loss, vasodilatory shock induced by cardio-pulmonary bypass, milrinone-induced vasodilatory shock in congestive heart failure, hepatorenal syndrome type I, anaphylactic shock, or cardiovascular instability induced by brain death, wherein said method comprises administering to an animal, including human, patient of a therapeutically effective amount of a compound as outlined above.

In a further embodiment the invention relates to a method for treatment of hypotension in severe sepsis, acute respiratory distress syndrome or acute lung injury, wherein said method comprises administering to an animal, including human, patient of a therapeutically effective amount of a compound as outlined above.

In another embodiment the invention relates to a method for treatment of inadequate tissue oxygenation, shock induced by metformin intoxication, mitochondrial disease or cyanide poisoning, vascular leak syndrome induced by interleukin-2 or other cytokines, denileukin diftitox or other immunotoxins, or ovarian hyperstimulation syndrome, hypertension induced by end-stage renal disease, severe burns, thermal injury, irritable bowel disease, ulcerative colitis, reperfusion injury, infant respiratory distress syndrome, severe acute respiratory syndrome, ascites, vasodepressor syncope, including vasovagal syncope, postural hypotension with syncope or neurocardiogenic syncope, toxic shock syndrome, idiopathic systemic capillary leak syndrome (Clarkson's disease), wherein said method comprises administering to an animal, including human, patient of a therapeutically effective amount of a compound as outlined above.

The typical dosage of the compounds used according to the present invention varies within a wide range and will depend on various factors such as the individual needs of each patient and the route of administration. The dosage administered by infusion is generally within the range of 0.01-200 mg/kg body weight per hour. A physician of ordinary skill in the art will be able to optimise the dosage to the situation at hand.

The abbreviations used are:
AcBuc 1-aminocyclobutane-1-carboxylic acid
Ala(cPe) cyclopentylalanine
Boc tert-butoxycarbonyl
BOP benzotriazol-1-yloxy trisdimethylaminophosphonium hexafluorophosphate
Bu butyl
Cha cyclohexylalanine
Dbu 2,4-diaminobutyric acid
DCC N,N'-dicyclohexylcarbodiimide
DCHA dicyclohexylamine
DCM dichloromethane
DIAD diisopropyl diazodicarboxylate
DIC N,N'-diisopropylcarbodiimide
DIEA N,N-diisopropyl-N-ethylamine
DMF N,N-dimethylformamide
Fm 9-fluorenylmethyl
Fmoc 9-fluorenylmethoxycarbonyl
HOBt 1-hydroxybenzotriazole
HPLC high performance liquid chromatography
i iso
Mmt 4-methoxytrityl
Mob p-methoxybenzyl
MS mass spectrometry
Orn ornithine
Ph phenyl
Pr propyl
PyBOP benzotriazol-1-yloxy trispyrrolidinephosphonium hexafluorophosphate
o-NBS-Cl 2-nitrobenzenesulfonyl chloride
OT oxytocin
Rt retention time
t tert
TFA trifluoroacetic acid
TIS triisopropylsilane
TMOF trimethylorthoformate
TPP triphenylphosphine
Trt trityl
VT vasotocin, [Ile$^3$]vasopressin
Z benzyloxycarbonyl Unless otherwise specified L-amino acids were used, and conventional amino acid terminology is adhered to.

EXPERIMENTAL

Synthesis

Amino acid derivatives and resins were purchased from commercial providers (Novabiochem, Bachem, Peptide International and PepTech Corporation). Other chemicals and solvents were provided from Sigma-Aldrich, Fisher Scientific and VWR.

The compounds herein were synthesised by standard methods in solid phase peptide chemistry utilising both Fmoc and Boc methodology. Unless otherwise provided, all reactions were performed at room temperature. In addition to the references cited supra, the following standard reference literature provides further guidance on general experimental set up, as well as on the availability of required starting material and reagents:

Kates, S. A., Albericio, F., Eds., *Solid Phase Synthesis. A Practical Guide*, Marcel Dekker, New York, Basel, 2000;
Stewart, J. M., Young, J. D. *Solid Phase Synthesis*, Pierce Chemical Company, 1984;
Bisello, et al., *J. Biol. Chem.* 1998, 273, 22498-22505; and
Merrifield, *J. Am. Chem. Soc.* 1963, 85, 2149-2154.

Purity of the synthesized peptide may be determined by analytical reversed phase HPLC. Structural integrity of the peptides may be confirmed using amino acid analysis and electrospray mass spectrometry.

The peptides synthesised by Fmoc methodology were cleaved with a TFA/TIS/H$_2$O 96/2/2 (v/v/v) solution, and cleavage in Boc methodology was accomplished with 90% HF/10% anisole (v/v) solution. Disulfide bridge (ring) formation was achieved by oxidation of linear peptides dissolved in 10% TFA (aq) with iodine. Peptides were purified by preparative HPLC in triethylammonium phosphate buffers (aq). The compounds were finally converted to acetate salts using conventional HPLC methodology. The fractions with a purity exceeding 97% were pooled and lyophilised.

Synthesis of peptides with alkylated side chain in position no. 8 (e.g. compound no. 4):

The peptides were assembled with Fmoc methodology. The diamino acid residue in position no. 8 was introduced with an acid labile (i.e. removable with a solution containing 1-2% TFA) protecting group, such as methoxytrityl (Mmt; see Barlos, K. et al. in *Peptides* 1992, Schneider, C. H., Eberle, A. N., Eds., ESCOM Science Publishers B.V., 1993, pp 283-284). Resin bound peptide was treated with a DCM/

TIS/TFA 93/5/2 (v/v/v) solution for the Mmt group removal. Reductive alkylation with acetone/NaBH(OAc)$_3$ provided the N-isopropyl peptide.

To avoid undesirable N,N-dialkylation in reductive alkylation in the above procedure, which may occur when straight chain alkyl aldehydes are used, an alternative was developed, wherein after the Mmt removal the amino group was first derivatised with 2-nitrobenzenesulfonyl chloride (o-NBS-Cl; see Fukuyama, T.; Jow, C.-K.; Cheung, M. *Tetrahedron Lett.* 1995, 36, 6373-6374). The resulting sulphonamide was then alkylated with an appropriate alcohol under conventional Mitsunobu reaction conditions, typically utilising TPP/DIAD in 1,2-dimethoxyethane (Mitsunobu, O. *Synthesis* 1981, 1-28). The o-NBS-Cl group was subsequently removed with 5% potassium thiophenolate in DMF, after which the peptide was cleaved from the resin.

Synthesis of peptides with N-alkylated side chain in position no. 4:

The peptides were assembled with Boc methodology. The residue in position no. 4 was introduced in the sequence as Boc-Asp(OFm)-OH. After complete peptide assembly the side chain protection was removed with 30% piperidine in DMF. The resulting free carboxylic group was converted to the desired amide by coupling with an appropriate amine mediated by PyBOP or BOP/DIEA. The N-terminal Boc group was then removed, followed by HF cleavage, cyclisation and purification by HPLC.

Table 1 lists the compounds prepared by the above procedure together with the determined (vide infra) EC$_{50}$ (median effective concentration) expressed in nanomol/L. $R_3$, $R_4$, $R_5$, $R_6$, $R_7$ and $R_6$ are H for all compounds except compound 4, where $R_6$ is isopropyl instead of H. For the listed compounds m is 1, except where $R_1$ and $R_2$ are part of an alicyclic structure (formed together with the a carbon of the amino acid in position no. 2) exemplified here as 1,1-cyclobutyl.

TABLE 1

Compounds prepared with the formula (I)

| Substituent | | | | | | |
|---|---|---|---|---|---|---|
| $R_1$ | $R_2$ | X | n | p | EC$_{50}$ | Denoted |
| H | CH$_2$X | cyclohexyl | 2 | 2 | 0.27 | 1 (SEQ ID NO: 1) |
| H | CH$_2$X | cyclopentyl | 2 | 2 | 0.80 | 2 (SEQ ID NO: 2) |
| 1,1-cyclobutyl | — | | 2 | 2 | 0.94 | 3 (SEQ ID NO: 3) |
| H | CH$_2$X | cyclohexyl | 1 | 3 | 10.7 | 4 (SEQ ID NO: 4) |
| H | CH$_2$X | i-propyl | 2 | 2 | 12.0 | 5 (SEQ ID NO: 5) |
| 1,1-cyclobutyl | — | | 1 | 3 | 7.93 | 6 (SEQ ID NO: 6) |
| H | CH$_2$X | cyclopentyl | 1 | 3 | 7.70 | 7 (SEQ ID NO: 7) |
| H | CH$_2$X | cyclohexyl | 1 | 3 | 0.75 | 8 (SEQ ID NO: 8) |
| 1,1-cyclobutyl | — | | 1 | 2 | 14.8 | 9 (SEQ ID NO: 9) |
| H | CH$_2$X | cyclopentyl | 1 | 2 | 17.8 | 10 (SEQ ID NO: 10) |
| H | CH$_2$X | t-butyl | 2 | 2 | 9.93 | 11 (SEQ ID NO: 11) |
| H | CH$_2$X | cyclohexyl | 1 | 2 | 2.28 | 12 (SEQ ID NO: 12) |
| | | N/A | | | 82.1 | terlipressin |

The following detailed examples are provided to further illustrate the synthesis:

Compound 4; [Cha$^2$, Asn$^4$, Orn (i-Pr)$^8$]VT:

The amino acid derivatives used were Boc-Cys(Trt)-OH, Fmoc-Cha-OH, Fmoc-Ile-OH, Fmoc-Gln(Trt)-OH, Fmoc-Asn(Trt)-OH, Fmoc-Cys(Trt)-OH, Fmoc-Pro-OH, Fmoc-Orn(Mmt)-OH and Fmoc-Gly-OH. Analytical HPLC was performed on a Waters 600 Liquid Chromatograph using a Vydac C18, 5μ 4.6×250 mm, column at a flow rate of 2 ml/min. Preparative HPLC was performed on a Waters 2000 Liquid Chromatograph using a Prepak 47×300 mm cartridge at a flow rate of 100 ml/min. Final compound analysis was performed on a 1100 Agilent Liquid Chromatograph using a Vydac C18, 5μ 2.1×250 mm, column at a flow rate of 0.3 ml/min. Mass spectra were recorded on a Finnigan MAT spectrometer.

The fully protected peptide resin was synthesised on an Applied Biosystems 9050 Peptide Synthesiser starting from 0.4 g (0.1 mmol) of Tentagel-S-RAM resin (Peptides International). DIC/HOBt mediated single couplings with a 4-fold excess of amino acid derivatives were performed. The Fmoc group was removed with 20% piperidine in DMF. Upon completion of the automated synthesis, the resin was transferred into a manual synthesis vessel and was treated with DCM/TIS/TFA 93/5/2 (v/v/v) solution (30 ml) for 2×1.5 hours for removal of the Mmt group. The resin was thoroughly washed with DCM and was subsequently suspended in 15 ml of 1,2-dichloroethane/TMOF 1:1 (v/v). 0.2 ml of acetone was then added followed by 0.6 g of NaBH(OAc)$_3$. The suspension was shaken overnight and the resin was washed with methanol, DMF and DCM and dried in vacuo. The resin was then treated with 30 ml of the TFA/TIS/H$_2$O 96/2/2 (v/v/v) solution for 1.5 hours and filtered off. The filtrate was evaporated and the crude linear peptide was precipitated with diethyl ether. The precipitate was immediately dissolved in 500 ml of 10% TFA (aq), and the peptide was oxidised by adding 0.1 M I$_2$ in methanol to the magnetically stirred solution until yellow color persisted. Excess of iodine was reduced with ascorbic acid. The reaction mixture was then cooled with crushed ice and pH was adjusted to about 5 by adding concentrated ammonia (aq). The mixture was loaded onto an HPLC column and purified using a triethylammonium phosphate buffer with pH 5.2. The compound was eluted with a gradient of acetonitrile. The fractions with a purity exceeding 97% were pooled, and the resulting solution was diluted with 2 volumes of water. The solution was reloaded onto the column which was then washed with 2 l of 0.1 M ammonium acetate (aq) and equilibrated with 2% acetic acid (aq). The compound was eluted with a fast (3%/min) gradient of acetonitrile. The fractions containing the desired product were pooled and lyophilised. 20.7 mg (20% yield) of white amorphous powder was obtained. HPLC: Rt=8.2 min, gradient: 30→50% B over 20 min, flow: 0.3 ml/min, t=40° C., solvent A 0.01% TFA (aq), solvent B 70% CH$_3$CN, 0.01% TFA (aq); Purity: 100%; MS (M+H$^+$): expected 1026.5, observed 1026.5.

Compound 3; [AcBuc$^2$,Dbu$^8$]VT:

The amino acid derivatives used were Boc-Cys(Mob)-OH, Boc-AcBuc-OH, Boc-Ile-OH, Boc-Gln-OH, Boc-Asn-OH, Boc-Pro-OH, Boc-Dbu(Z)—OH DCHA salt and Boc-Gly-OH, all purchased from Novabiochem and Bachem. HPLC and MS operations were performed as in the synthesis of 202256.

The fully protected peptide resin was manually synthesised starting from 0.6 g (0.4 mmol) of 4-methylbenzhydrylamine resin (Novabiochem). DCC, PyBOP or DIC/HOBt mediated single couplings with 2.5-fold excess of amino acid derivatives were employed. The Boc group was removed with 50% TFA in DCM containing 1% of m-cresol. The finished resin was washed with methanol, DMF and DCM and dried in vacuo. The peptide was cleaved from the resin by using 30 ml of anhydrous HF containing 3 ml of anisole at 0° C. for 90 minutes. The HF was evaporated off, and the crude linear peptide was washed with diethyl ether. The peptide was immediately dissolved in 200 ml of 25% acetonitrile/10% TFA (aq) and oxidised as described supra. The resulting mixture was loaded directly onto an HPLC column and purified using triethylammonium phosphate buffer at pH 2.3. Unless otherwise provided the subsequent steps were identical to the procedure for 202256. 80.6 mg (22% yield) of white amorphous powder was obtained. HPLC: Rt=7.3 min, gradient: 20→40% B over 20 min, flow: 0.3 ml/min, t=40° C., solvent A 0.01% TFA (aq), solvent B 70% $CH_3CN$, 0.01% TFA (aq); Purity: 99.6%; MS (M+H$^+$): expected 928.4, observed 928.3.

The other compounds were prepared by analogous variation of these synthetic procedures.

EXPERIMENTAL

Biological Testing

In Vitro Receptor Assays:

Agonist activity of compounds on the hV1a receptor was determined in a transcriptional reporter assay by transiently transfecting a hV1a receptor expression DNA into HEK-293 cells in concert with a reporter DNA containing intracellular calcium responsive promoter elements regulating expression of firefly luciferase. See Boss, V., Talpade, D. J., Murphy, T. J. *J. Biol. Chem.* 1996, May 3; 271(18), 10429-10432 for further guidance on this assay. Cells were exposed to serial dilutions of compounds diluted 10-fold per dose for 5 hours, followed by lysis of cells, determination of luciferace activity, and determination of compound efficacies and $EC_{50}$ values through non-linear regression. Arginine-vasopressin (AVP) was used as an internal control in each experiment, and compounds were tested in at least three independent experiments.

The results of the in vitro assays are depicted in table 1 supra. The $EC_{50}$ value given is the geometric mean expressed in nanomol/L (nM). Selectivity values are given as $EC_{50}$ ratios.

All references listed are to be regarded as an integral part of the present writ.

The invention claimed is:

1. A method of treating a condition comprising administering to an animal in need of such treatment a therapeutically effective amount of a compound having the formula (I):

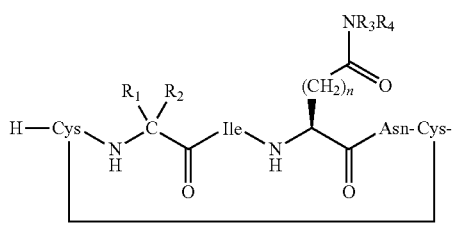

(I)

-continued

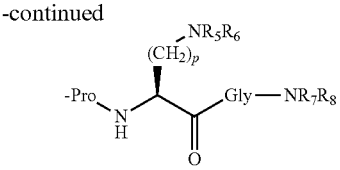

or a pharmaceutically acceptable salt thereof, wherein:
$R_1$ is H; and
$R_2$ is $(CH_2)_m$—X;
or $R_1$ and $R_2$ in combination with the carbon atom to which they are attached together form an acyclic structure that comprises from 3 to 8 carbon atoms;

m is selected from 0, 1, 2 and 3;
n is selected from 0, 1, 2, 3 and 4;
p is selected from 2, 3 and 4;
when m is 0, 2 or 3, X is selected from $C_{3-8}$-cycloalkyl and $C_{5-8}$-cycloalkenyl;
when m is 1, X is selected from $C_{3-8}$-cycloalkyl, $C_{5-8}$-cycloalkenyl, isopropyl and tert-butyl;
said alicyclic structure, $C_{3-8}$-cycloalkyl, and $C_{5-8}$-cycloalkenyl, optionally have at least one alkyl, O-alkyl or hydroxyl substituent;
$R_3$, $R_4$, $R_5$, $R_6$, $R_7$ and $R_8$ are each independently selected from H, alkyl, OH, O-alkyl and OC(O)-alkyl; and
alkyl is selected from $C_{1-6}$ straight and $C_{4-8}$ branched chain alkyl and optionally has at least one hydroxyl substituent; and
wherein the condition is selected from:
hypertensive gastropathy bleeding,
prolonged and severe hypotension,
intradialytic hypotension,
vasodilatory shock induced by cardiopulmonary bypass,
milrinone-induced vasodilatory shock in congestive heart failure,
anaphylactic shock,
cardiovascular instability induced by brain death,
acute respiratory distress syndrome,
acute lung injury,
shock induced by metformin intoxication, mitochondrial disease or cyanide poisoning, vascular leak syndrome induced by interleukin-2 or another cytokine, denileukin diftitox or another immunotoxin, or ovarian hyperstimulation syndrome,
hypertension induced by end-stage renal disease,
reperfusion injury,
infant respiratory distress syndrome,
ascites,
vasodepressor syncope, including vasovagal syncope, postural hypotension with syncope or neurocardiogenic syncope,
toxic shock syndrome,
inadequate tissue oxygenation, and
idiopathic systemic capillary leak syndrome (Clarkson's disease).

2. A method according to claim 1, wherein the condition is:
acute respiratory distress syndrome or
acute lung injury.

3. A method according to claim 1, wherein the condition is:
inadequate tissue oxygenation,
shock induced by metformin intoxication, mitochondrial disease or cyanide poisoning, vascular leak syndrome induced by interleukin-2 or another cytokine, denileukin diftitox or another immunotoxin, or ovarian hyperstimulation syndrome,
hypertension induced by end-stage renal disease,
reperfusion injury,
infant respiratory distress syndrome,
ascites,
vasodepressor syncope, including vasovagal syncope, postural hypotension with syncope or neurocardiogenic syncope,
toxic shock syndrome, and
idiopathic systemic capillary leak syndrome (Clarkson's disease).

4. A method according to claim 1, wherein $R_7$ and $R_8$ are H.

5. A method according to claim 1, wherein $R_3$ and $R_4$ are H.

6. A method according to claim 1, wherein n is 1 or 2.

7. A method according to claim 1, wherein alkyl is selected from methyl, ethyl, n-propyl, i-propyl, t-butyl and i-amyl.

8. A method according to claim 1, wherein X is cyclopentyl or cyclohexyl.

9. A method according to claim 1, wherein said alicyclic structure is a cyclobutyl structure.

10. A method according to claim 1, wherein the condition is:
hypertensive gastropathy bleeding,
prolonged and severe hypotension,
intradialytic hypotension,
vasodilatory shock induced by cardiopulmonary bypass,
milrinone-induced vasodilatory shock in congestive heart failure,
anaphylactic shock, or
cardiovascular instability induced by brain death.

11. A method according to claim 1, wherein the compound is a compound of the following formula:

(SEQ ID NO: 1)

H-Cys-Cha-Ile-Gln-Asn-Cys-Pro-Dbu-Gly-NH$_2$ or a pharmaceutically acceptable salt thereof.

12. A method according to claim 1, wherein the compound is a compound of the following formula:

(SEQ ID NO: 2)

H-Cys-Ala(cPe)-Ile-Gln-Asn-Cys-Pro-Dbu-Gly-NH$_2$ or a pharmaceutically acceptable salt thereof.

13. A method according to claim 1, wherein the compound is a compound of the following formula:

(SEQ ID NO: 3)

H-Cys-AcBuc-Ile-Gln-Asn-Cys-Pro-Dbu-Gly-NH$_2$ or a pharmaceutically acceptable salt thereof.

14. A method according to claim 1, wherein the compound is a compound of the following formula:

(SEQ ID NO: 4)

H-Cys-Cha-Ile-Asn-Asn-Cys-Pro-Orn(i-Pr)-Gly-NH$_2$ or a pharmaceutically acceptable salt thereof.

* * * * *

UNITED STATES PATENT AND TRADEMARK OFFICE
CERTIFICATE OF CORRECTION

PATENT NO. : 9,050,286 B2  
APPLICATION NO. : 12/673375  
DATED : June 9, 2015  
INVENTOR(S) : Regent LaPorte and Pierre J. M. Riviere Page 1 of 1

It is certified that error appears in the above-identified patent and that said Letters Patent is hereby corrected as shown below:

Title Page, Item (54) and in the Specification, Column 1, Line 1 (Title); Delete "VASOPRESSION" and insert -- VASOPRESSIN --.

Signed and Sealed this
First Day of March, 2016

Michelle K. Lee
*Director of the United States Patent and Trademark Office*